United States Patent [19]

Torstensson

[11] 4,438,654
[45] Mar. 27, 1984

[54] DEVICE FOR TAKING GROUND WATER SAMPLES IN SOIL AND ROCK

[76] Inventor: Bengt-Arne Torstensson, 34, Höjdvägen, S-186 00 Vallentuna, Sweden

[21] Appl. No.: 358,707

[22] Filed: Mar. 16, 1982

[30] Foreign Application Priority Data

Mar. 27, 1981 [SE] Sweden ................................. 8101989

[51] Int. Cl.³ ............................................. G01N 1/14
[52] U.S. Cl. .................................. 73/864.52; 166/264
[58] Field of Search ........... 73/864.52, 864.74, 863.23; 166/264

[56] References Cited

U.S. PATENT DOCUMENTS

| | | | |
|---|---|---|---|
| 3,374,678 | 3/1968 | McGuckin | 73/864.72 X |
| 3,490,288 | 1/1970 | Patnode | 73/863.23 |
| 3,862,576 | 1/1975 | Pogorski | 73/863.23 X |
| 4,063,460 | 12/1977 | Svensson | 73/863.52 |
| 4,329,883 | 5/1982 | Barnes | 73/864.52 |

Primary Examiner—Daniel M. Yasich
Attorney, Agent, or Firm—Burns, Doane, Swecker & Mathis

[57] ABSTRACT

This invention relates to a device for taking samples of ground water in soil and rock, comprising an at least partially evacuated sampling container of which the end facing downward in operative position is sealed air-tight by a first member of flexible material. The object of the invention is to improve the existing art for taking ground water samples in soil and rock. The device according to the invention renders it possible to take samples, which are hermetically sealed until they are analyzed in the laboratory. The device according to the invention is characterized, in that a second member of flexible material closes the upper end of the ground water sampler, and a two-sided cannula is movable in its longitudinal direction relative to the two members.

12 Claims, 5 Drawing Figures

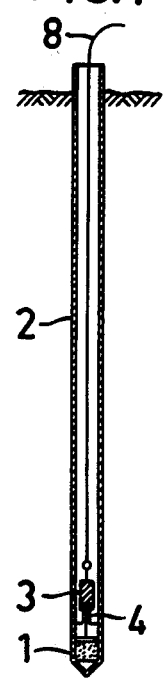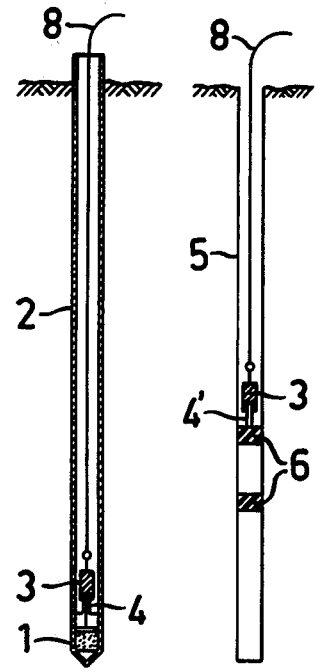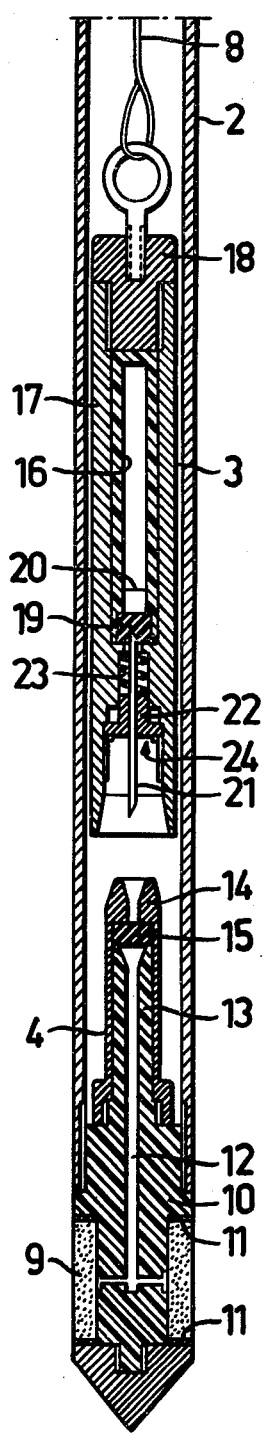

DEVICE FOR TAKING GROUND WATER SAMPLES IN SOIL AND ROCK

BACKGROUND AND SUMMARY OF THE PRESENT INVENTION

This invention relates to a device for taking samples of ground water in soil and rock, comprising a sampling container, of which the end facing downward in operation is closed by a first member of flexible material.

There is in many connections a great demand for being able to take representative samples of ground water in soil and rock, for example at the examination of:

(1) impurities and their spread
(2) water acidification
(3) water corrosivity, etc.

The methods used at present for taking such samples show great deficiencies in many respects. By contact with the oxygen in air, for example, the sample can oxidize, whereby its original chemical properties can be changed. Furthermore, at the digging of test pits for taking ground water samples, uncertainty arises, due to ground water leaking in, whether the sample taken is representative of the sampling level in question.

The present invention has the object to improve the technique used at present for ground water sampling in soil and rock. The new device renders it possible to take samples, which are hermetically closed until being analysed in the laboratory. The new device also provides the possibility to extract samples of ground water from relatively fine-grained soils, such as silt and clay.

BRIEF DESCRIPTION OF THE DRAWINGS

An embodiment of the invention is described in the following, with reference to the accompanying drawings, in which FIGS. 1 and 2 are schematic views of the basic design of two embodiments of the invention, FIG. 3 is a sectional view on an enlarged scale through a device according to the invention, where the parts comprised in the device are not coupled together.

DETAILED DESCRIPTION OF THE PREFERRED EMBODIMENTS

Figure 4:
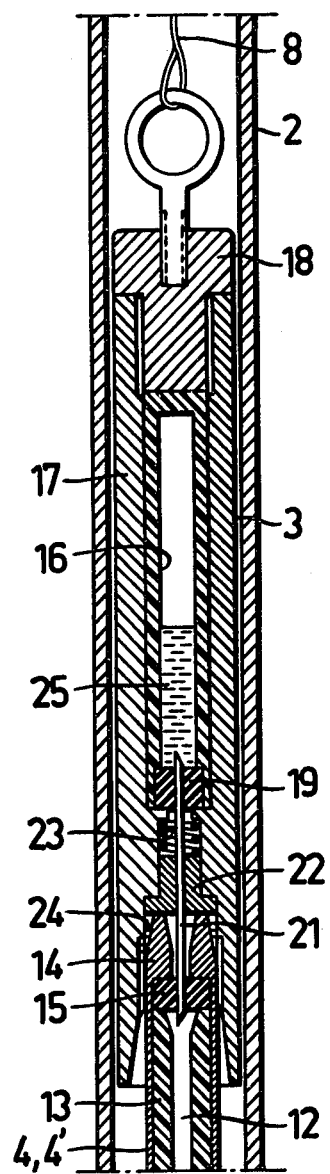
FIG. 4 is a partial cross sectional view on an enlarged scale the device according to the invention in a state coupled together.

At the taking of samples in soil, see FIG. 1, the device consists of a filter tip 1, which has been installed in the soil and is connected to a pipe 2 extending upward all the way to the ground surface. At the taking of ground water samples a sampler 3 is lowered within the pipe and connected sealingly to a nipple 4 in the filter tip. At the sampling in rock, see FIG. 2, first a hole 5 is drilled in the rock, whereafter the predetermined sampling level is sealed according to known art from the remaining part of the drill hole by means of elastic sealing sleeves 6, of which the upper one is provided with a nipple 4' for connection to the sampler 3. When the desired sample has been obtained, the sampler is pulled up by means of a rope or wire 8.

The basic design of the filter tip 1 as known shown in FIG. 1 corresponds to that according to SE-PS No. 411656. This filter tip has, among others, the characterizing feature that it comprises, as shown in FIG. 3, a filter 9, preferably of ceramic material, which partially encloses a probe tip 10, preferably of thermoplastic material. It is important that both the filter and the probe tip are manufactured of stable and inactive material, in order to prevent contamination of the ground water, for example by chemical precipitation or stress corrosion. The filter with its end surfaces abuts sealing washers of an elastic material 11. In the probe tip, a passageway 12 extends from the filter 9. The passageway 12 opens into a nipple 13, which is closed by a sleeve comprising a sealing member 15 of an elastomer or flexible member such as crude rubber. The sealing member 15, which may be penetrated by a pointed cannula, acts as a self-closing quick coupling.

The sampler 3 is characterized in that it comprises a sampling cylinder 16, which is mounted in a sleeve 17, which upwardly is provided with a nut 18 closing the sleeve. To the nut a rope or wire 8 is attached for lowering or pulling up the sampler in the pipe 2 or rock drill hole 5. The sampling sleeve 16 is closed by a plug 19 manufactured of an elastomer or crude rubber. The diameter of the plug is chosen so that at its mounting in the sleeve 16 it is imparted with a compression and prestressing in radial direction. The plug 19, which may be penetrated by a cannula, has the function of a self-closing quick coupling. Prior to its mounting in the sleeve 17, the sampling cylinder shall be evacuated of air. This is carried out, for example according to known art, by penetrating a cannula through the plug 19 and thereafter connecting the cannula to a so-called water suction exhaust or some other type of evacuation means. By this method, a negative pressure close to absolute vacuum can be established in the sampling cylinder. When the cannula is being pulled out of the sampling cylinder, the plug 19 automatically will close the same, whereby the negative pressure will remain in the sampling cylinder. When the requirements on purity are high, the sampling cylinder can be disinfected before the evacuation. When the water sample is required not to contain too great an amount of suspended particles, a filter 20 can be provided in the sampling cylinder.

The sampler also comprises a two-sided cannula 21 with pointed ends, which is mounted on a holder 22 movably mounted in the sleeve 17. The holder 22 on the side facing to the sampling cylinder abuts a resilient member 23, for example a steel spring or a porous elastic material. At the mounting of the cannula holder 22 in the sleeve 17, a certain prestress is applied to the resilient member 23 by a jamb nut 24 engaging with the sleeve 17. When the resilient member 23 is being prestressed by means of the nut 24, the end of the cannula 21 facing toward the sampling cylinder partially will penetrate the plug 19 and thereby establish sealing of the cannula.

The prepared sampler is lowered in the pipe 2 or rock drill hole 5. The lower end of the sampler having inwardly a conic portion, it is centered on the nipple 4 of the filter tip or the nipple 4' of the elastic sealing sleeve. By action of the dead weight of the sampler, or by extra weights thereon, the cannula 21 first will penetrate the sealing member 15 in the nipple 4 or the nipple 4' and thereafter the plug 19 in the sampling cylinder. It is important from a sampling aspect, that the cannula first penetrates the sealing member 15 in the filter tip 1 or the sealing sleeve 6 before its other end entirely penetrates the plug 19 in the sampling cylinder. This requirement is met simply by applying a suitable prestressing to the resilient member 23 and by selecting both suitable thicknesses and suitable material for the sealing members 15 and 19. By action of the negative pressure in the sampling cylinder 16, liquid—ground water—is sucked into the same via the filter 9 and passageway 12. FIG. 4 shows the sampler 3 coupled together with the nipple 4 alternatively nipple 4'. The Figure shows the sampling cylinder partially filled with liquid 25. When the sampler is being removed from the nipple, first the cannula by action of the resilient member 23 will be drawn into the plug 19, whereby the sampling cylinder is closed. Thereafter the cannula will be drawn out of the sealing member 15 in the nipple 4 or 4'. In this way a hermetically closed liquid sample in the sample cylinder is obtained.

Figure 5:
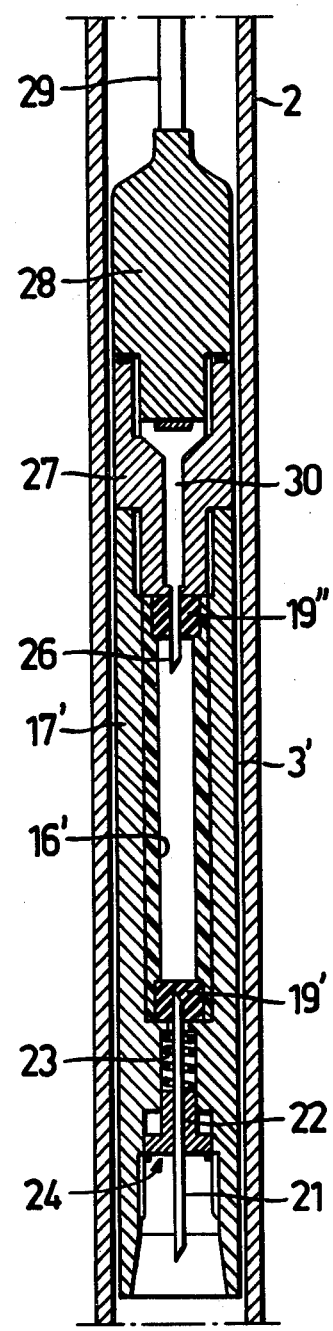
FIG. 5 is a partial cross sectional view on an enlarged scale an alternative embodiment of the device according to the invention.

FIG. 5 shows an alternative embodiment of the sampler 3'. In this embodiment the sampling cylinder 16' is provided at both end surfaces with sealing plugs 19',19" of an elastomer or crude rubber. The sampling cylinder is mounted in a sleeve 17'. In the upper sealing plug on the sampling cylinder preferably a cannula 26 is penetrated which via an intermediate piece 27 including a passageway 30 sealingly communicates with an electric pressure transducer 28. The sampler 3' preferably is lowered in the pipe 2 by an electric cable 29 to the pressure transducer. The sampling cylinder 16' is evacuated of air in the same way as described for the device in FIG. 3. The embodiment of the sampler according to FIG. 5 has the object to render it possible to observe the filling procedure in the sample cylinder at the sampling. This is carried out simply by reading the change of the pressure in the sampling cylinder. This pressure change preferably is recorded automatically by a recorder. On the basis of the information obtained from the time progress for the filling of the sample cylinder, calculations also can be made of the water permeability of the soil or rock in question.

When only determinations of the permeability of the soil or rock are desired, the procedure, of course, may be such that the sample cylinder 16' partially is filled with liquid and partially with compressed gas. When the sampler 3' is connected to the nipple 4 or the nipple 4', the liquid in the sample cylinder, due to the overpressure of the compressed gas, will be pressed out to the surrounding soil or rock. When in the same way as described above the time progress for the pressure change in the sample cylinder is measured by the pressure transducer 28, information can be obtained for calculating the water permeability of the soil or rock in question.

The invention is not restricted to the embodiments described above, but can freely be varied within the scope of the attached claims.

What I claim is:

1. A device for taking at least one ground water sample in soil and rock, comprising a movable element having an at least partially evacuated sampling container, an end of the container facing downward being sealed air-tight by a first member of a flexible material, the device further including a ground water collector, a second member of flexible material closing an upper end of the ground water collector, and a cannula with two pointed ends arranged between said first and second members, means for selectively moving the cannula in its longitudinal direction relative to the two members for selectively penetrating the first and second members with a respective one of the ends for transferring a ground water sample from the collector to the sampling container.

2. The device as defined in claim 1, wherein the means for selectively moving the cannula includes a holder, the cannula being fixedly mounted in the holder which is movable relative to the container and arranged below the first member in the operative position of the container.

3. The device as defined in claim 2, further comprising means operatively associated with the holder for exerting a counterforce when the holder is moved in a direction toward the first member of flexible material.

4. The device as defined in claim 3, wherein the means for exerting a counterforce comprises a compression spring.

5. The device as defined in claim 1 or 2, wherein the ground water sampler is a filter tip on which a nipple is attached, the second member of flexible material being mounted in the nipple.

6. The device as defined in claim 5, wherein the sampling container is located in a sleeve which is downwardly open in an operative position and is intended to receive the nipple.

7. The device as defined in claim 1 or 2, wherein the ground water sampler is a drill hole in which a sealing sleeve of elastic material is attached, a nipple being attached on the sleeve, and the second member of elastic material being mounted in the nipple.

8. The device as defined in claim 7, wherein the sampling container is located in a sleeve which is downwardly open in an operative position and is intended to receive the nipple.

9. The device as defined in claim 1, wherein the sampling container includes a filter.

10. The device as defined in claim 1, wherein the sampling container is connected to a pressure transducer.

11. The device as defined in claim 1, wherein the members of flexible material are comprised of an elastomer.

12. The device as defined in claim 1, wherein the members of flexible material are comprised of crude rubber.

* * * * *